US007666196B1

(12) United States Patent
Miles

(10) Patent No.: US 7,666,196 B1
(45) Date of Patent: Feb. 23, 2010

(54) KNOT TYING DEVICE AND METHOD

(76) Inventor: Christopher R. Miles, 220 S. 800 West, Lewiston, UT (US) 84320

( * ) Notice: Subject to any disclaimer, the term of this patent is extended or adjusted under 35 U.S.C. 154(b) by 501 days.

(21) Appl. No.: 11/602,567

(22) Filed: Nov. 20, 2006

Related U.S. Application Data

(60) Provisional application No. 60/738,692, filed on Nov. 21, 2005, provisional application No. 60/785,248, filed on Mar. 22, 2006.

(51) Int. Cl.
*A61B 17/04* (2006.01)
(52) U.S. Cl. .......................................... 606/144; 289/2
(58) Field of Classification Search ................ 606/139, 606/144, 148; 289/2, 5, 12, 17, 18.1
See application file for complete search history.

(56) References Cited

U.S. PATENT DOCUMENTS

| | | | | |
|---|---|---|---|---|
| 2,455,833 A * | 12/1948 | Trombetta | ................. | 606/139 |
| 3,106,417 A * | 10/1963 | Clow | ........................... | 289/17 |
| 3,131,957 A * | 5/1964 | Musto | ........................ | 289/17 |
| 3,177,021 A * | 4/1965 | Benham | ..................... | 289/17 |
| 3,752,516 A * | 8/1973 | Mumma | ..................... | 289/17 |
| 3,806,860 A * | 4/1974 | Flammini | .................. | 439/817 |
| 4,328,605 A * | 5/1982 | Hutchison et al. | ......... | 24/115 G |
| 4,881,302 A | 11/1989 | Lee | | |
| 5,184,798 A | 2/1993 | Wilson | | |
| 5,197,166 A | 3/1993 | Meier et al. | | |
| 5,336,230 A * | 8/1994 | Leichtling et al. | ........... | 606/148 |
| 5,454,821 A * | 10/1995 | Harm et al. | ................. | 606/148 |
| 5,527,323 A * | 6/1996 | Jervis et al. | ................. | 606/148 |
| 5,562,684 A * | 10/1996 | Kammerer | .................. | 606/139 |
| 5,571,117 A * | 11/1996 | Ahn | ........................... | 606/139 |
| 5,716,368 A * | 2/1998 | de la Torre et al. | .......... | 606/148 |
| 5,741,280 A * | 4/1998 | Fleenor | ..................... | 606/148 |
| 5,746,753 A * | 5/1998 | Sullivan et al. | ............. | 606/147 |
| 5,749,898 A * | 5/1998 | Schulze et al. | .............. | 606/228 |
| 5,971,447 A * | 10/1999 | Steck, III | ..................... | 289/17 |
| 6,010,515 A * | 1/2000 | Swain et al. | ................. | 606/148 |
| 6,200,329 B1 * | 3/2001 | Fung et al. | .................. | 606/232 |

(Continued)

OTHER PUBLICATIONS

Cabela'S, "Moodus Sports Tool", www.cabelas.com/cabelas/en/templates/links/link.jsp?id=0001323310861a&type=p..., Oct. 10, 2006, 2 pages.

(Continued)

*Primary Examiner*—(Jackie) Tan-Uyen T Ho
*Assistant Examiner*—Son Dang
(74) *Attorney, Agent, or Firm*—Robert L. Lundstrom

(57) ABSTRACT

A knot tying device for tying knots including an inner rod having a longitudinal slot extending between the two open ends from an outer diameter to a hollow center. An hollow cylinder is disposed on the inner rod and has a longitudinal slot extending between the two open ends from an outer diameter to a hollow center. A cord clamp is formed between the hollow cylinder and the inner rod, and secures a cord to an end of the outer hollow cylinder. A cord winding cylinder is rotatably disposed on the inner cylinder and has a cord catch and a longitudinal slot extending between the two open ends from an outer diameter to a hollow center. The cord catch can catch a cord secured by the cord clamp and can wind the cord around the outer hollow cylinder.

11 Claims, 12 Drawing Sheets

U.S. PATENT DOCUMENTS

| | | | | |
|---|---|---|---|---|
| 6,221,084 B1 | * | 4/2001 | Fleenor | 606/148 |
| 6,808,349 B1 | | 10/2004 | Boling | |
| 7,416,556 B2 | * | 8/2008 | Jackson | 606/232 |
| 2005/0228475 A1 | * | 10/2005 | Keeble et al. | 623/1.11 |

OTHER PUBLICATIONS

Cabela'S Cinch Tie Brass Knot Tyer, www.cabelas.com/cabelas/en/templates/links/link.jsp;jsessionid=O5YHT3IVDAFG..., Aug. 31, 2006, 2 pages.

Lake Products Company—Product Detail Page "The Fisherman's Knot Tying Tool- Charger Lures", www.knottying.com/detail.asp?Product_ID=001, Aug. 31, 2006, 2 pages.

Koehler Industries "Cinch Tie Knot Tyer" "Cinch Tie The Original Brass Knot Tyer" www.cinchtie.com/Cinch_tie_knot_tyer.htm, Aug. 31, 2006, 3 pages.

Orvis Sporting Traditions since 1856 "Cinch tie instructions" pp. 1-18, The Orvis Company Manchester Vermont.

Lake Products Company "The Fisherman's Knot-Tying Tool by Charger" Instruction booklet, pp. 1-32.

* cited by examiner

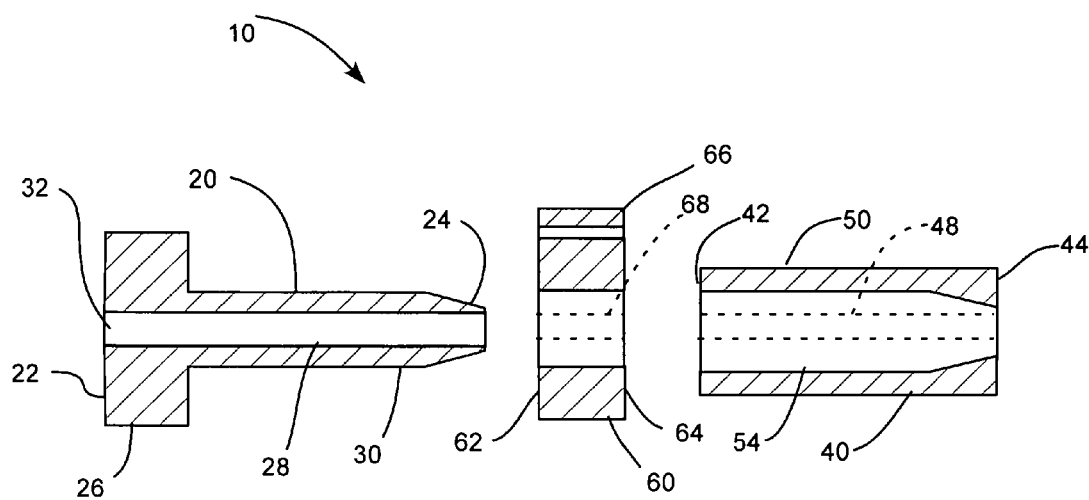
FIG. 3
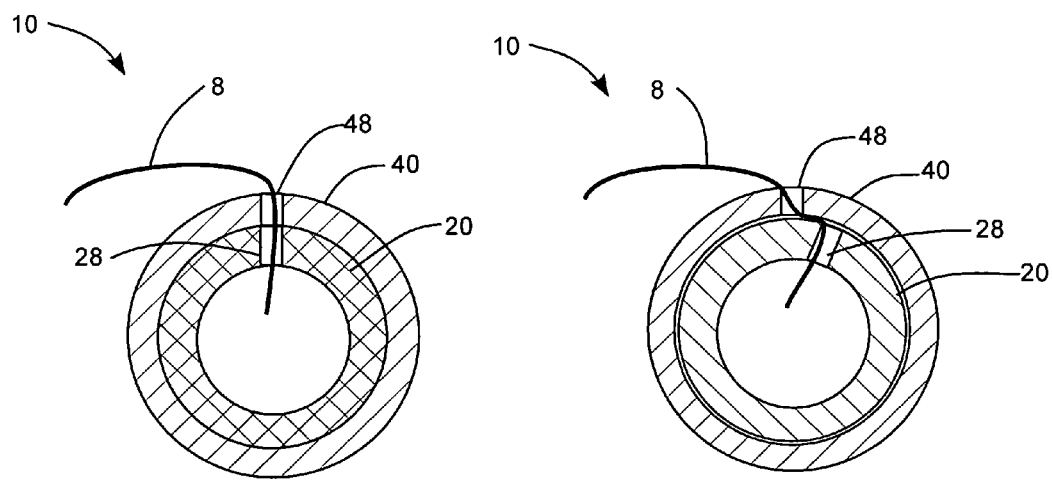
FIG. 4
FIG. 5

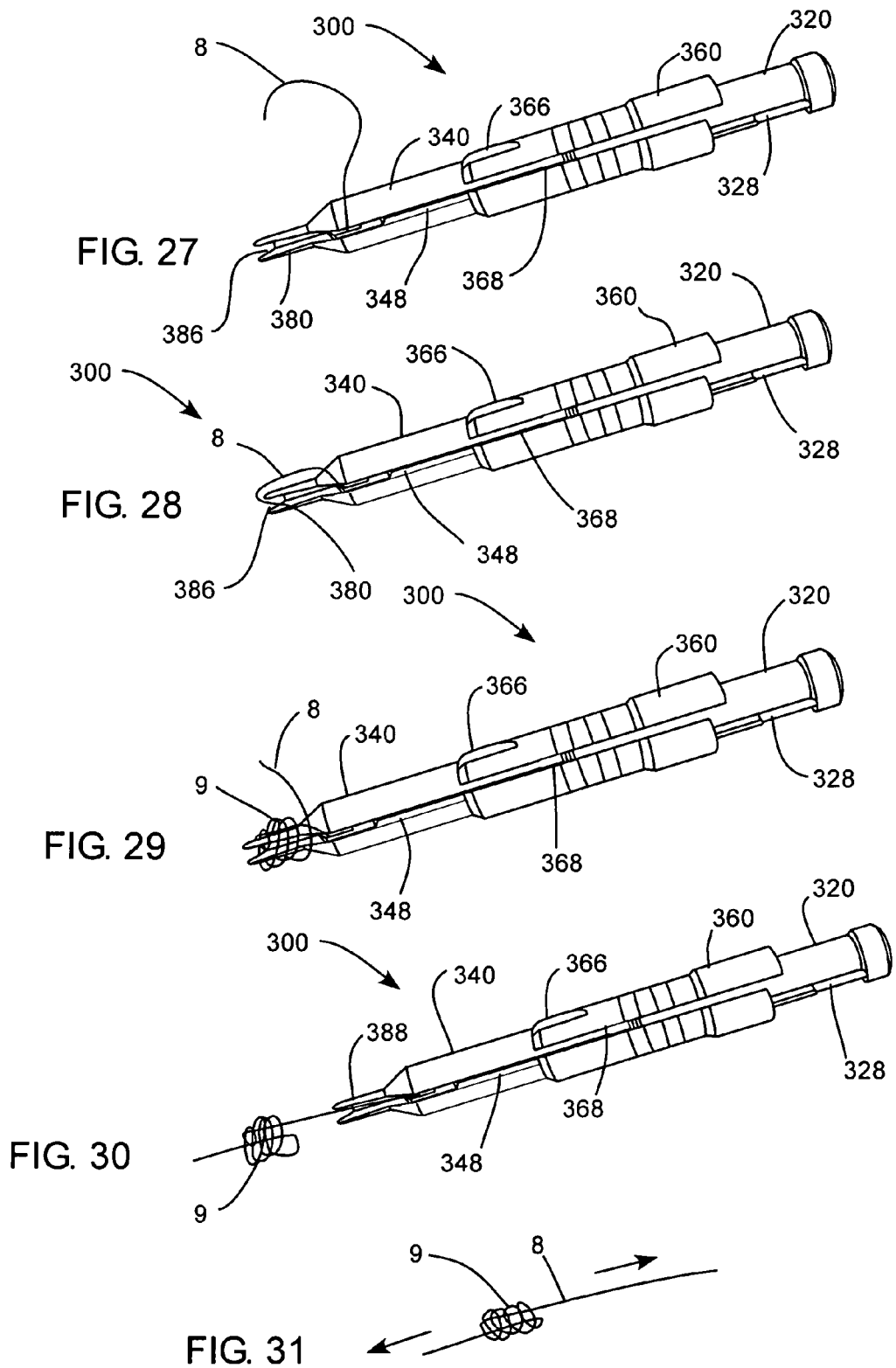

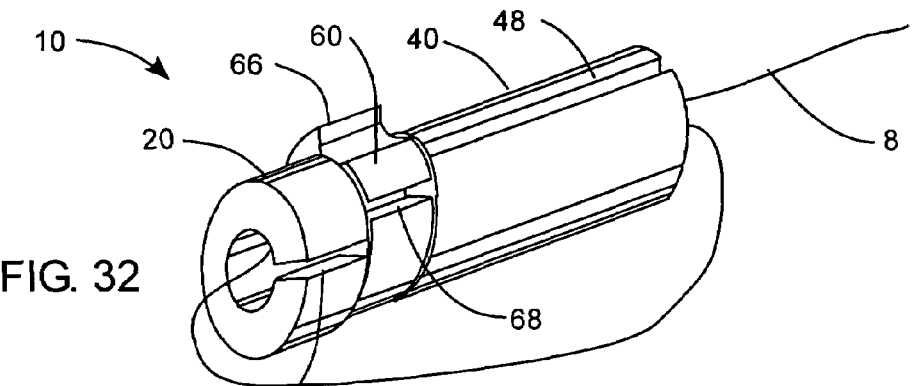
FIG. 32
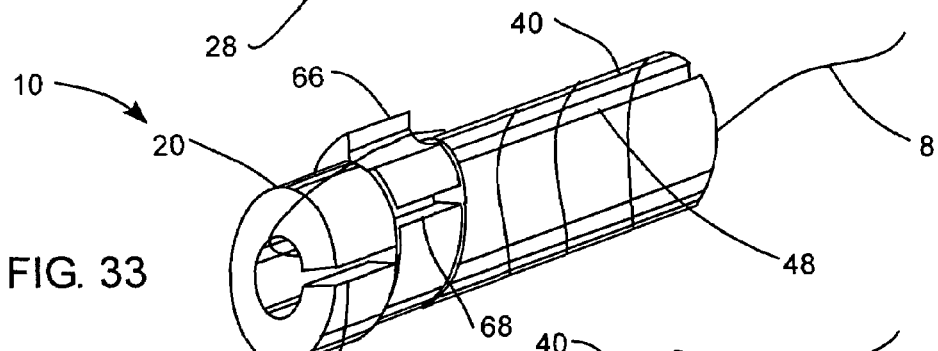
FIG. 33
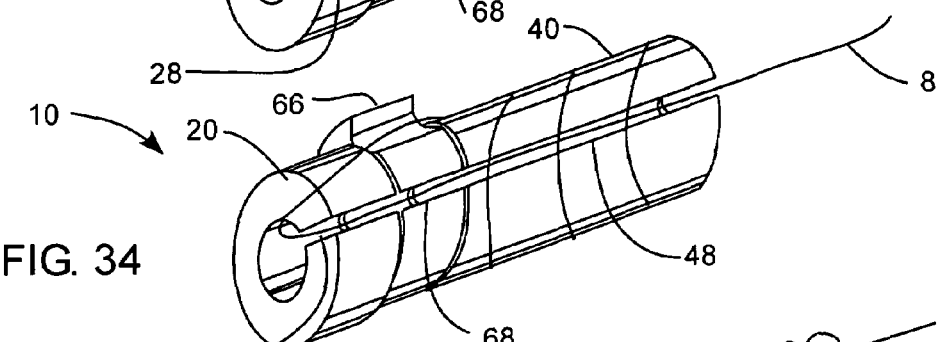
FIG. 34
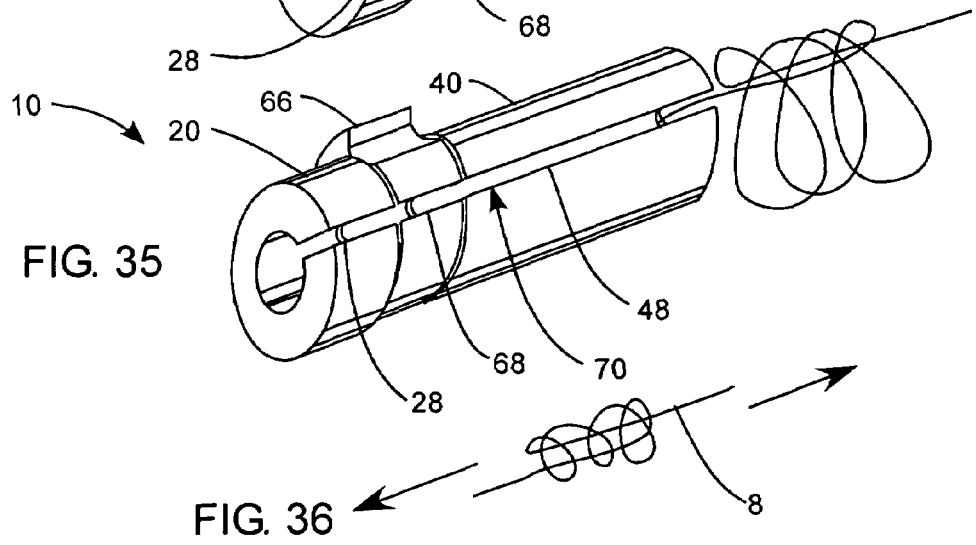
FIG. 35
FIG. 36

KNOT TYING DEVICE AND METHOD

PRIORITY CLAIM

This application claims priority to U.S. Provisional Application 60/738,692, filed Nov. 21, 2005, and to U.S. Provisional Application 60/785,248, filed Mar. 22, 2006, which are herein incorporated by reference in their entirety for all purposes.

BACKGROUND OF THE INVENTION

1. Field of the Invention

The present invention relates generally to knot tying devices.

2. Related Art

Knot tying devices are often used to provide assistance in tying knots that join two cords together, or tying knots around an object, such as a fish hook or fly. Typically, these devices are small handheld implements that have various geometric features around which a cord may be wound.

The knots these devices most commonly assist in tying are so called "nail knots" and "blood knots", though other knots can also be tied. Nail and blood knots are good for attaching a cord to an object or another line because the chord is wrapped in a series of loops around the object or line and also around a segment of the chord itself. Thus, when tension is applied to the cord the loops tighten around the object and the segment of cord so that both the object and cord segment are held fast and the knot is prevented from loosening.

Knot tying devices that assist in tying nail and blood knots usually have a place where an end of the cord can be held, and a hole or groove that a segment of the cord can extend through. After the cord is placed through the groove, the cord is wrapped around the knot tying device in several sequential loops so that a helical winding is formed on the device around the segment of cord contained in the groove. An object, such as a fish hook or a second line, may be placed in the groove so that the loops of the helical winding extend around the cord and the object or line. The two ends of the cord are pulled to tighten the knot and the knot is then removed from the tying device. After the device is removed the two ends of the cord are further tightened complete the knot.

Winding the loops to form the helical coil on these devices is tedious and problematic. Usually the user must keep a finger on the windings to keep them from unraveling, overlapping, or getting tangled. Furthermore, it is difficult and time consuming to maintain a consistent wrapping tension on the loops which creates a risk of overlapping and entanglements of the helical windings. Moreover, winding the cord around the knot tying device requires a sufficient length of cord to hold with the free hand and wrap the cord around the knot tying device. Such long lengths of cord can twist during the winding process causing the cord to tangle up with itself.

SUMMARY OF THE INVENTION

It has been recognized that it would be advantageous to develop a knot tying device with an internal clamp for securing a cord to the knot tying device. Additionally, it has been recognized that it would be advantageous to develop a knot tying device with a rotatable winding cylinder for creating relatively consistently shaped and tensioned windings in a knot. Furthermore it has been recognized that it would be advantageous to develop a knot tying device with alignable slots to facilitate removal of knots from the knot tying device.

The invention provides knot tying device for tying knots in a cord including an inner rod having an aperture sized and shaped to receive a cord. A hollow cylinder can be rotatably disposable on the inner rod. The hollow cylinder can have an interior sized and shaped to receive the inner rod therein, and an aperture extending from an outer surface of the hollow cylinder to the interior. The aperture can be sized and shaped to receive the cord. The outer surface of the hollow cylinder can be configured to wind a cord. The inner rod can be positionable in the interior of the hollow cylinder to selectively align and misalign the aperture in the inner rod with respect to the aperture in the hollow cylinder such that a cord extending through the aperture in the hollow cylinder to the aperture in the inner rod can be clamped between the inner rod and the hollow cylinder when the aperture in the inner rod is misaligned with the aperture in the hollow cylinder.

In another aspect, the present invention also provides for a knot tying device for tying knots in cord including an inner rod, having a longitudinal slot. An intermediate hollow cylinder can be rotatably disposable on the inner rod, and can have a longitudinal slot extending from an outer diameter to a hollow interior. The intermediate hollow cylinder can be rotatable on the inner rod to selectively align or misalign the slot in the inner rod with respect to the slot in the hollow cylinder to form a cord clamp therebetween when the slots are misaligned. A cord winding cylinder can be rotatably disposable on the intermediate hollow cylinder and longitudinally slidable thereon. A cord catch can be disposed on the cord winding cylinder and can catch the cord secured between the inner rod and the intermediate hollow cylinder and wind the cord around the outer hollow cylinder.

The present invention also provides for a method for forming a knot using a knot tying device. The method includes placing an inner rod with an aperture and a longitudinal slot into a hollow cylinder having a corresponding longitudinal slot. The hollow cylinder can be rotatably disposed on the inner rod to align or misalign the aperture and the longitudinal slots. The inner rod can be rotated within the hollow cylinder to align the aperture in the inner rod and the longitudinal slot in the hollow cylinder. A cord can be placed through the longitudinal slot in the hollow cylinder and into the aperture in the inner rod. The hollow cylinder can be rotated with respect to the inner rod to misalign the aperture in the inner rod and the longitudinal slot in the hollow cylinder so as to clamp the cord between the inner rod and an interior of the hollow cylinder. The cord can be extended around the hollow cylinder and into a notch in a tip cylinder of the hollow cylinder with a segment of the cord extending longitudinally along the tip cylinder. The cord can be wound around the hollow cylinder to forming loops. The loops can form a helical winding circumscribing the segment of cord extending longitudinally along the tip cylinder. The longitudinal slots of the inner rod and the hollow cylinder can be aligned to form a continuous longitudinal slot extending longitudinally along the knot tying device. The cord can be pushed through the aligned longitudinal slots from an end opposite the tip end toward the tip end. The loops can be slid off the hollow cylinder. The hollow cylinder can rotated with respect to the inner rod to unclamp the cord, and the cord can be tensioned to tighten the helical winding about the segment of the cord circumscribed therein.

Additional features and advantages of the invention will be apparent from the detailed description which follows, taken in conjunction with the accompanying drawings, which together illustrate, by way of example, features of the invention.

BRIEF DESCRIPTION OF THE DRAWINGS

FIG. 3 is an exploded cross section view of the knot tying device of FIG. 1;

FIG. 4 is a cross section end view of the knot tying device of FIG. 1, shown with a cord extending through aligned slots of an inner rod and a hollow cylinder;

FIG. 5 is a cross section end view of the knot tying device of FIG. 1, shown with a cord extending through and clamped by misaligned slots of an inner rod and a hollow cylinder;

FIGS. 27-31 illustrate steps in a method for forming a knot using a knot tying device in accordance with an embodiment of the present invention; and FIGS. 32-36 illustrate steps in a method for forming a knot using a knot tying device in accordance with another embodiment of the present invention.

DETAILED DESCRIPTION

Figure 1:
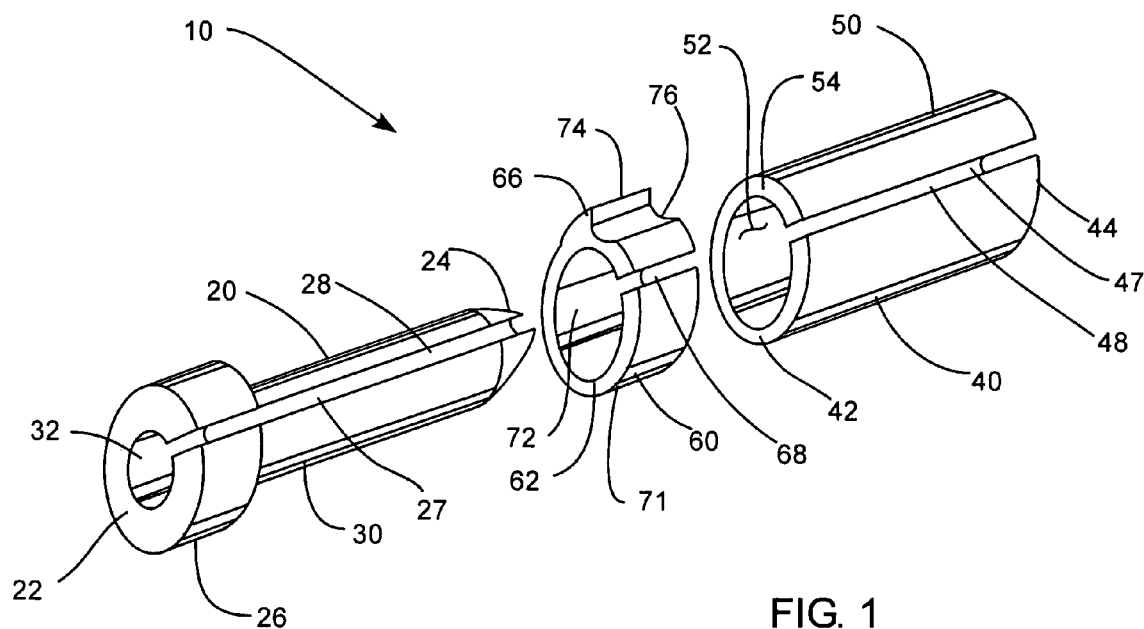
FIG. 1 is an exploded perspective view of a knot tying device in accordance with an embodiment of the present invention.

Reference will now be made to the exemplary embodiments illustrated in the drawings, and specific language will be used herein to describe the same. It will nevertheless be understood that no limitation of the scope of the invention is thereby intended. Alterations and further modifications of the inventive features illustrated herein, and additional applications of the principles of the inventions as illustrated herein, which would occur to one skilled in the relevant art and having possession of this disclosure, are to be considered within the scope of the invention.

The present invention provides for a device that is useful in tying knots such as so called "nail knots" or "blood knots." The device can be held in one hand and a cord can be manipulated around the device by the other hand. The device can consist of an inner rod, an hollow cylinder, and a winding cylinder. The inner rod, hollow cylinder, and winding cylinder each have a longitudinal slot that extends the length of each and provides access to the inside of knot tying device. The hollow cylinder can fit on the inner rod, and the winding cylinder can fit on the hollow cylinder and the inner rod. The winding cylinder can freely rotate on the inner cylinder. The winding cylinder can include a cord catch, such as a protruding flange, that can capture the cord in order to twist the cord around the hollow cylinder.

In use, a cord can be inserted into the slot of the inner rod and clamped between the hollow cylinder and the inner rod so that the cord is held fast and the hollow cylinder is restricted from moving on the inner rod. The winding cylinder can be rotated so that the cord catch catches the cord and winds the cord around the hollow cylinder to form loops or windings on the hollow cylinder. When several loops or windings have been created on the hollow cylinder, the free end of the clamped cord can be brought around the outside of the device and run back through the slot of the inner rod. The loops can be then slid off the hollow cylinder so that the loops circumscribe two segments of the cord. In this way, as tension is applied to the two ends of the cord, the loops tighten on the two segments to form a helical winding around the cord. Objects, such as fish hooks, or other cords, such as leader line, can be placed inside the loops before being tightened and, thus, can also be tightened into the helical winding and held fast by the knot.

Figure 2:
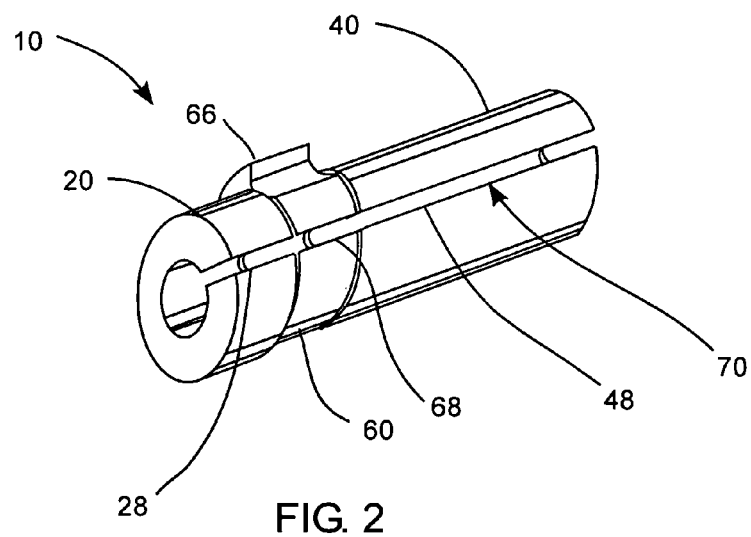
FIG. 2 is an assembled perspective view of the knot tying device of FIG. 1.

As illustrated in FIGS. 1-3, a knot tying device indicated generally at 10, in accordance with the present invention is shown for use in tying knots around an object or another cord. The knot tying device 10 can have an inner rod 20, an outer hollow cylinder 40, and a cord winding cylinder 60.

The inner rod 20 can have a head end 22 and tail end 24, and have a head portion 26 that protrudes around the head end 22. The inner rod 20 can also have an aperture 27 that is sized and shaped to receive an end of a cord 8. For example, the aperture can be a longitudinal slot 28 extending between the two ends 22 and 24 from an outer diameter 30 to an approximate center 32 of the inner rod 20.

The outer hollow cylinder 40 can be operably disposed on the inner rod 20. Specifically, the hollow cylinder 40 can have an interior hollow center 52 sized and shaped to slip onto the inner rod 20 forming a near zero clearance fit between the hollow cylinder and the inner rod. The hollow cylinder 40 can be open on two ends 42 and 44, and have an aperture 47 extending from an outer surface or diameter 54 of the hollow cylinder to the interior hollow center 52. The aperture 47 can be sized and shaped to receive the cord through the aperture. For example, the aperture 47 can be a longitudinal slot 48 extending between the two open ends from an outer diameter 50 to a hollow center 52.

The hollow cylinder 40 can form a cord clamp with the inner rod 20. Specifically, the inner diameter 54 of the hollow cylinder 40 can be slightly smaller than the outer diameter 30 of the inner rod 20. In this way, the inner rod 20 can be positionable within the interior hollow center 52 of the hollow cylinder 40, and a cord 8 can be placed between the inner rod and hollow cylinder, so as to trap, pinch, or clamp the cord between the inner rod and hollow cylinder.

The cord 8 can be clamped between the inner rod 20 and the hollow cylinder 40 in a variety of ways. For example, the cord 8 can be clamped between the inner rod 20 and hollow cylinder 40 by positioning the inner rod so as to selectively align and misalign the aperture 27 in the inner rod 20 with respect to the aperture 47 in the hollow cylinder 40. When aligned, the cord 8 can be placed through the apertures 27 and 47, as illustrated in FIG. 4, and the apertures can then be misaligned in order to trap the cord between the inner rod 20 and the hollow cylinder 40, as illustrated in FIG. 5.

Figure 6:
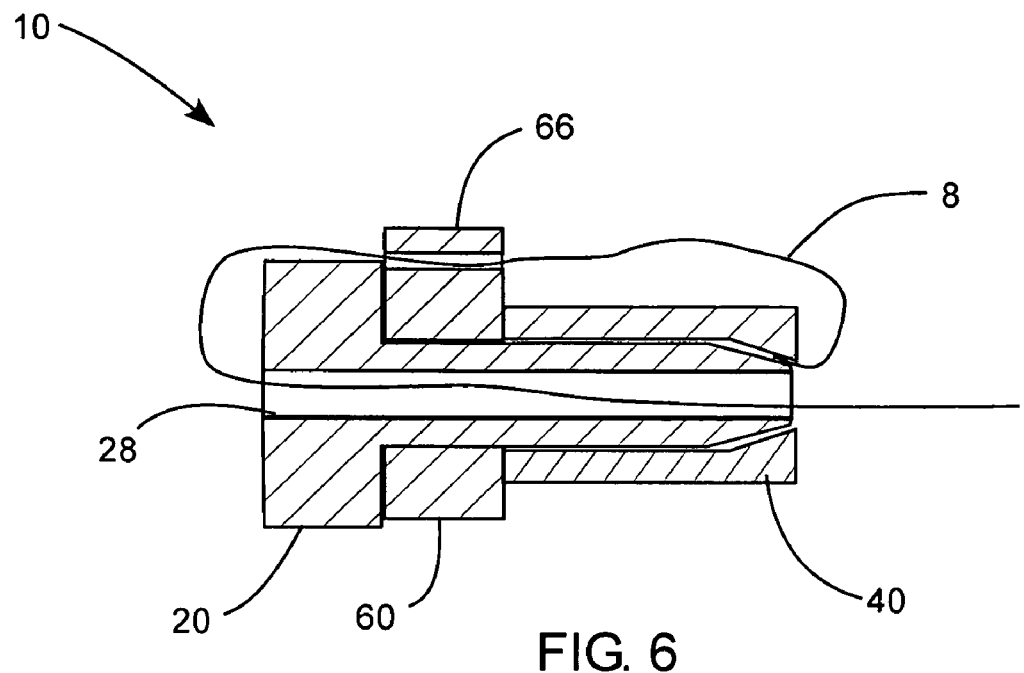
FIG. 6 is an assembled cross section view of the knot tying device of FIG. 1, shown with a cord clamped between a hollow cylinder and an inner rod.

Referring to FIG. 6, in another example, the cord 8 can be placed in an open end 44 of the hollow cylinder 40 and adjacent the inner diameter 54 of the hollow cylinder 40 such that when the hollow cylinder is placed on the inner rod 20 the cord 8 is clamped between the outer diameter 30 of the inner rod and the inner diameter 54 of the outer hollow cylinder, as illustrated in FIG. 6. Thus, the hollow cylinder 40 can be operable on the inner rod 20 to secure a cord between the inner cylinder and the hollow cylinder by placing the cord 8 in the hollow center 52 of the hollow cylinder and then pressing, rotating or twisting the inner rod into the hollow cylinder so as to pinch or clamp the cord between the rod and the cylinder.

It will be appreciated that having the cord 8 clamped on one end of the cord not only secures the cord from movement within the inner rod 20, but also provides tension to the cord when a completed knot is removed from the knot tying device 10 and tightened to form a cinched knot. Advantageously, the tension provided by the cord clamp, allows the user to pull the other end of the cord, thereby placing both ends of the cord in tension. Thus, the tension in the cord during winding, removal, and tightening of the knot is consistent across the knot which helps to form a knot with more consistently shaped and tensioned windings.

The knot tying device 10 can also have a cord winding cylinder 60. The cord winding cylinder 60 can be rotatably disposed on the hollow cylinder 40 and the inner rod 20 adjacent the head portion 26. The cord winding cylinder 60 can be open on two ends 62 and 64 and can have a cord catch 66. The cord winding cylinder 60 can also have a longitudinal slot 68 extending between the two open ends 62 and 64 from an outer diameter 71 to a hollow center 72. The cord winding cylinder can freely rotate about the inner rod.

The cord catch 66 can rotate with the cord winding cylinder 60 and can catch the cord 8 secured by the cord clamp. The cord catch 66 can then wind the cord 8 around the hollow cylinder 40 as the cord winding cylinder 60 is rotated about the inner rod 20. In this way, loops can be formed on the hollow cylinder 40 from the cord that is secured by the cord clamp. In one aspect, the cord catch 66 can be a longitudinal protrusion 74 located adjacent a longitudinal groove 76 as shown in FIGS. 1-3. In another aspect, the cord catch can be an indentation cut into the cord winding cylinder.

It will be appreciated that the cord winding cylinder 60 can be rotated about the hollow cylinder 40 to form the helical windings, or the cord winding cylinder can be held by the user's fingers, and the hollow cylinder 40 and inner rod 20 can be rotated inside the cord winding cylinder. In either case, the cord 8 can be caught by the cord catch 66 and helical windings can be formed about a portion of the hollow cylinder 40.

The inner rod 20, the hollow cylinder 40, and the cord winding cylinder 60 can be rotated with respect to one another in order to align the longitudinal slots 28, 48, and 68. In this way, a continuous slot, indicated generally at 70 (FIG. 70) can be formed between the two ends 12 and 14 of the knot tying device 10. The slots 28, 48, and 68 can be sized and shaped to allow the cord 8 to pass through the continuous slot 70 and escape the knot tying device 10.

Figure 7:
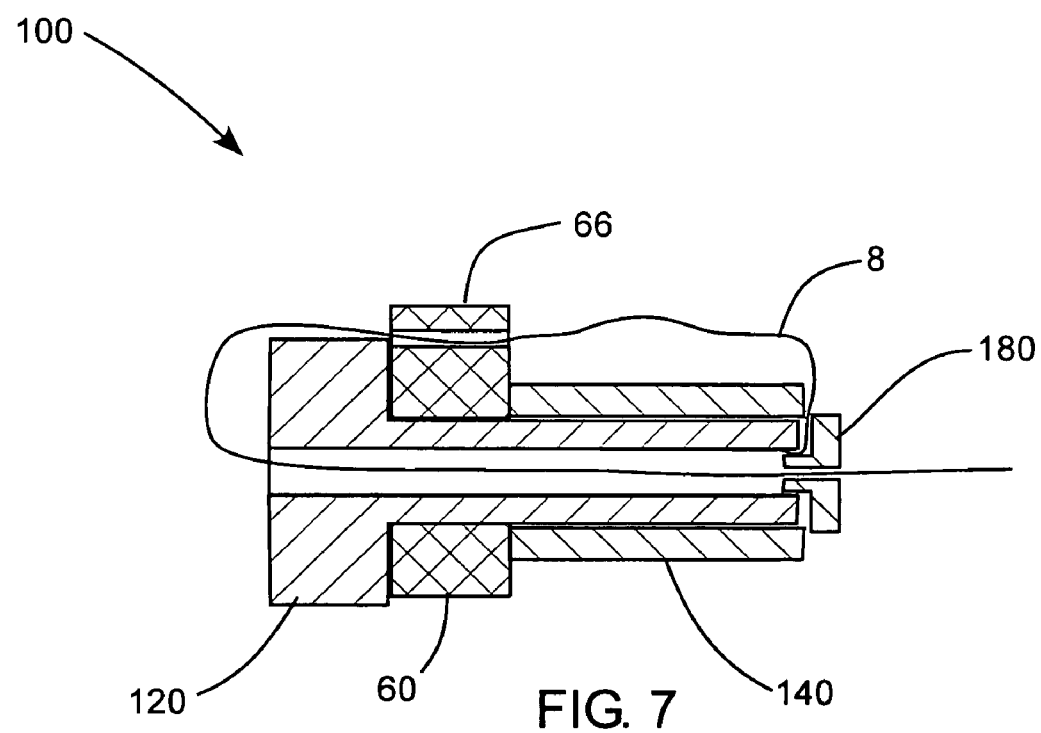
FIG. 7 is an assembled cross section view of a knot tying device in accordance with another embodiment of the present invention, shown with a cord clamped between a hollow cylinder and a cord clamping cylinder.

Referring to FIG. 7, a knot tying device, indicated generally at 100, is shown in accordance with another embodiment of the present invention. The knot tying device 100 is similar in many respects to the knot tying device 10 described above and shown in FIGS. 1-6. Additionally, the knot tying device 100 can have a cord clamp that includes a hollow plug or cord clamp cylinder 180 sized and shaped to fit into the inner rod 120. The cord clamp cylinder 180 can have an outer diameter slightly smaller than the inner diameter of the hollow cylinder 140. Thus, when the cord clamp cylinder 180 is pressed into the hollow cylinder 140, a clamping point is created between the cord clamp cylinder 180 and the hollow cylinder 140. In this way, a cord 8 can be placed between the cord clamp cylinder 180 and the hollow cylinder 140, so that when the cord clamp cylinder is placed in the hollow cylinder, the cord 8 is clamped between the cord clamp cylinder 180 and hollow cylinder 140 and, thus, secured top the knot tying device 100.

There are several advantages to clamping and preventing the securing the cord to the knot tying device. For example, having one end of the cord secured allows the user to work on the knot without having to hold two loose ends of cord, thereby usually freeing one of the user's hands. Additionally, with the cord clamped, tension can be uniformly distributed in the cord as the cord is wound around the hollow cylinder during formation of the knot.

Figure 8:
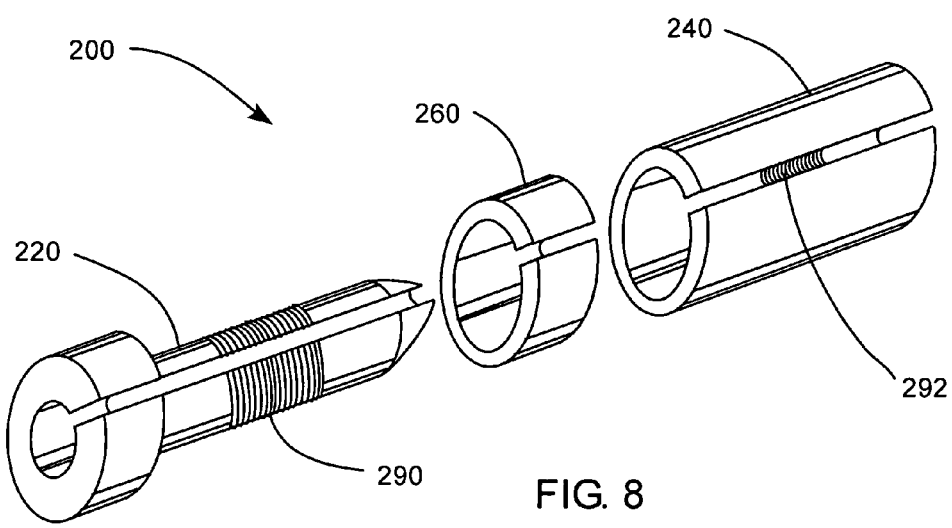
FIG. 8 is an exploded perspective view of a knot tying device in accordance with another embodiment of the present invention.
Figure 9:
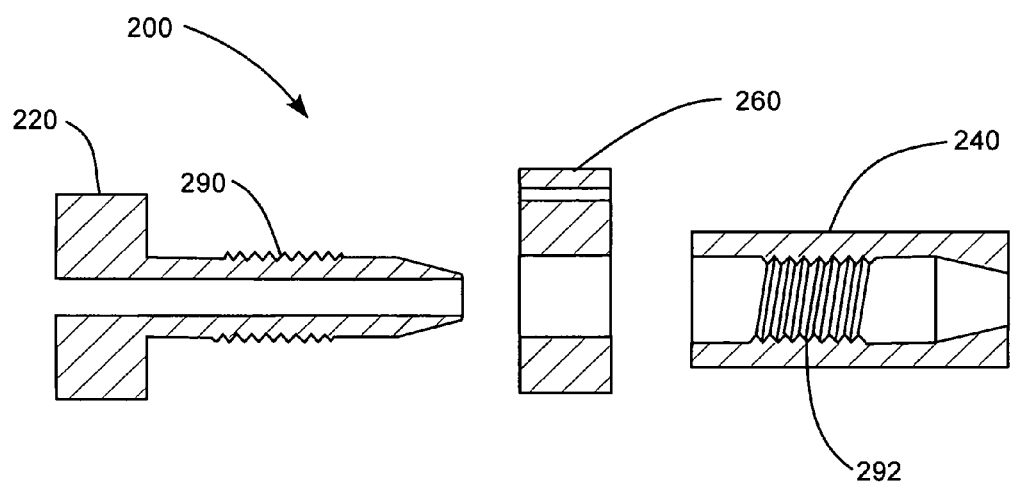
FIG. 9 is an exploded cross section view of the knot tying device of FIG. 6.

Referring to FIGS. 8-9, a knot tying device, indicated generally at 200, is shown in accordance with another embodiment of the present invention. The knot tying device 200 is similar in many respect to the knot tying devices 10 and 100 described above and shown in FIGS. 1-7. The knot tying device 200 can have an inner rod 220, a hollow cylinder 240, and a cord winding cylinder 260.

The inner rod 220 can have an external screw thread 290 on the outer diameter 254 of the inner rod. The hollow cylinder 240 can have an internal screw thread 292 on the inner diameter 252 of the hollow cylinder. The internal screw thread 292 of the hollow cylinder 240 can screw onto the external screw thread 290 of the inner rod 220. In this way, the hollow cylinder 240 can be attached to the inner rod and can be rotatably advanceable to tighten the screw threads 292 and 290 together so that the hollow cylinder 240 and inner rod 220 have restricted longitudinal movement with respect to one another.

There are several advantages to having the hollow cylinder 240 restricted from moving with respect to the inner rod 220. For example, when the hollow cylinder 240 is clamping a cord against the inner rod 220 any movement of the hollow cylinder with respect to the inner rod will loosen the clamp on the cord and result in uneven tension on the cord as the winding cylinder 280 is winding the cord around the outer hollow cylinder. This, of course, can result in misshapen windings that can tangle when tightening the knot. Additionally, when the hollow cylinder 240 is secured to the inner rod 220 the cord winding cylinder 260 can more uniformly and efficiently form loops around the outer diameter of the hollow cylinder since the tension in the cord is kept constant.

Referring to FIGS. 10-17, illustrated are various cord winding cylinders that can be used on the knot tying devices 10 and 100. It will be appreciated that numerous configurations could be used for the cord catch and that those shown in FIGS. 8-14 are merely representative of such cord catches. Other cord catch configurations can be conceived by those skilled in the art and will work equally as well so long as they catch the cord and wind it around the outer hollow cylinder.

Figure 10:
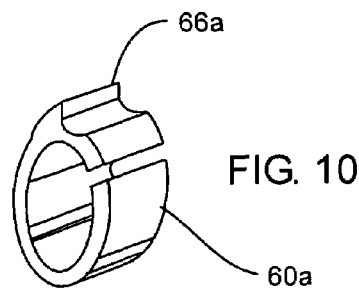
FIG. 10 is a perspective view of a cord winding cylinder in accordance with an embodiment of the present invention.
Figure 11:
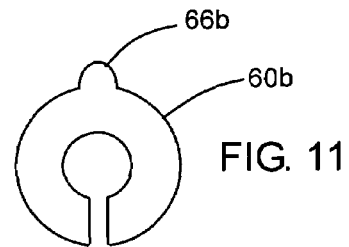
FIG. 11 is a top view of a cord winding cylinder in accordance with an embodiment of the present invention.
Figure 12:
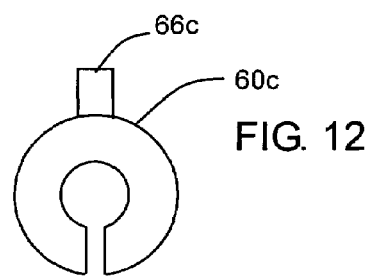
FIG. 12 is a top view of a cord winding cylinder in accordance with an embodiment of the present invention.
Figure 13:
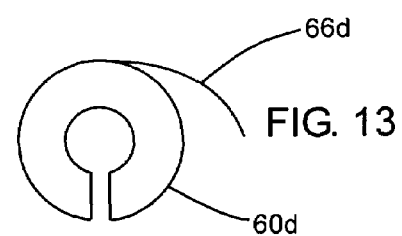
FIG. 13 is a top view of a cord winding cylinder in accordance with an embodiment of the present invention.
Figure 14:
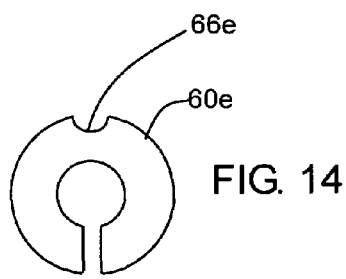
FIG. 14 is a top view of a cord winding cylinder in accordance with an embodiment of the present invention.
Figure 15:
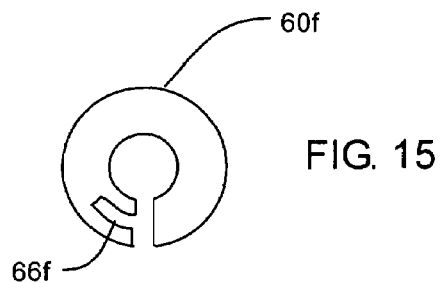
FIG. 15 is a top view of a cord winding cylinder in accordance with an embodiment of the present invention.
Figure 16:
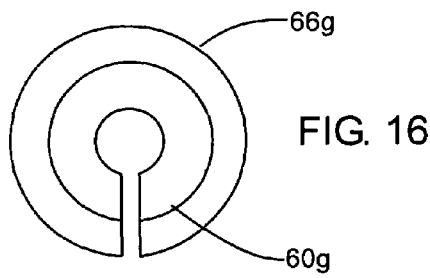
FIG. 16 is a top view of a cord winding cylinder in accordance with an embodiment of the present invention.
Figure 17:
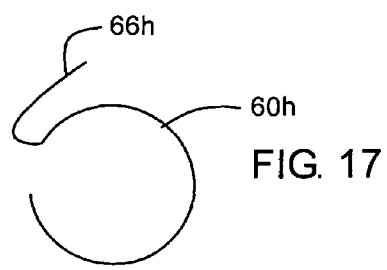
FIG. 17 is a top view of a cord winding cylinder in accordance with an embodiment of the present invention.

Thus, in one aspect, FIG. 10 shows the cord winding cylinder 60*a* with a longitudinal protrusion and longitudinal groove for the cord catch 66*a* as described above. In another aspect, FIG. 11 shows a cord winding cylinder 60*b* with only a protrusion formed longitudinally on the cord winding cylinder as the cord catch 66*b*. In another aspect, FIG. 12 shows a cord winding cylinder 60*c* including a pin 66*c* pressed into the cord winding cylinder and extending away from the outer diameter of the cord winding cylinder. In yet another aspect, FIG. 13 shows a cord catch 66*d* that is a wire hook pressed into the cord winding cylinder 60*d* and extends away from the outer diameter of the cord winding cylinder. In yet another aspect, FIG. 14 shows a cord catch 66*e* that is a groove extending longitudinally along a length of the cord winding cylinder 60*e*. In yet another aspect, FIG. 15 shows a cord catch 66*f* that is a flange integrally formed in the cord winding cylinder 60*f* and concentric with an inner diameter of the cord winding cylinder. In yet another aspect, FIG. 16 shows a cord catch 66*g* that is a press ring disposable over the cord winding cylinder 60*g*. The press ring can be sized and shaped to clamp a cord between the press ring and the cord winding cylinder. In yet another aspect, FIG. 17 shows a cord catch 66*h* that is a wire that can be sized and shaped to snap onto and rotate around the outer diameter of the inner rod.

As illustrated in FIGS. 18-28, a knot tying device, indicated generally at 300, is shown in accordance with another embodiment of the present invention. The knot tying device 300 is similar in many respects to the knot tying devices 10, 100 and 200 described above and shown in FIGS. 1-9. The knot tying device 300 can have an inner rod 320, and a hollow cylinder 340.

Figure 18:
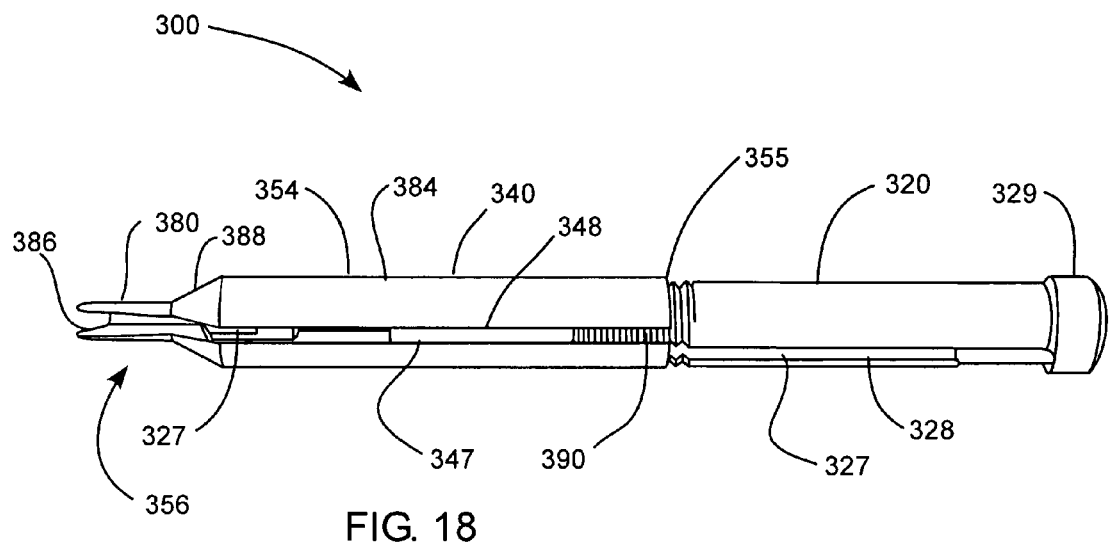
FIG. 18 is an assembled perspective view of a knot tying device in accordance with another embodiment of the present invention.
Figure 19:
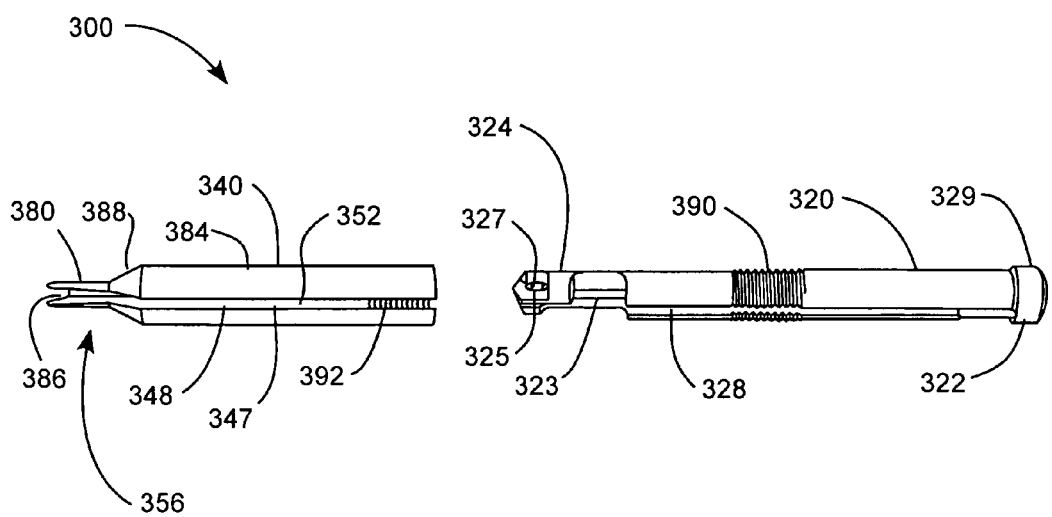
FIG. 19 is an unassembled perspective view of the knot tying device of FIG. 18.
Figure 20:
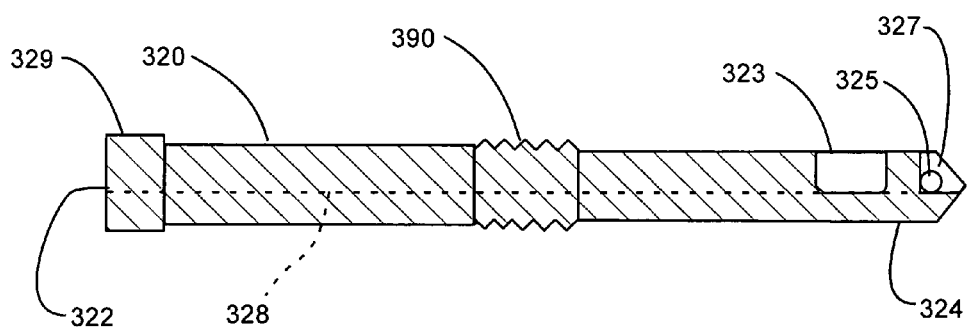
FIG. 20 is a cross section view of an inner rod of the knot tying device of FIG. 18.
Figure 21:
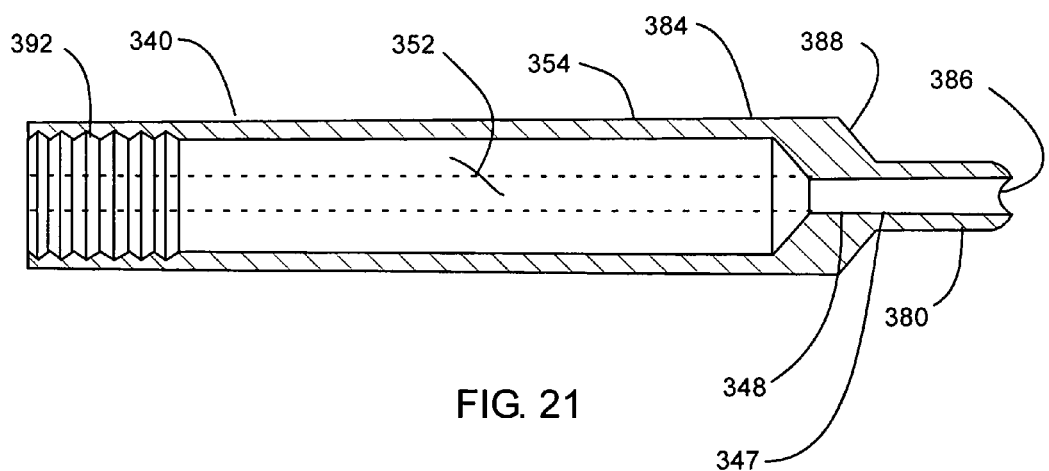
FIG. 21 is a cross section view of a hollow cylinder of the knot tying device of FIG. 18.
Figure 22:
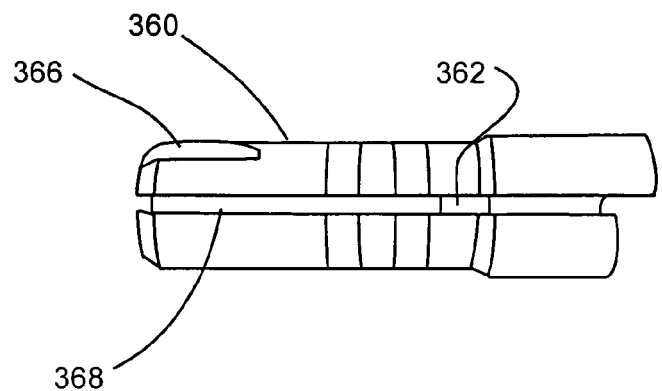
FIG. 22 is a side view of a cord winding cylinder of the knot tying device of FIG. 18.
Figure 23:
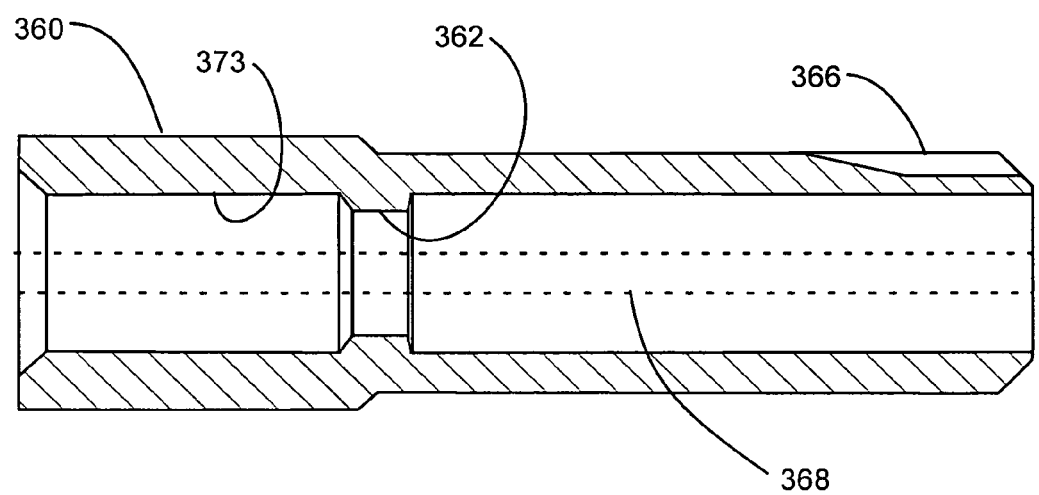
FIG. 23 is a cross section side view of the cord winding cylinder of FIG. 22.
Figure 24:
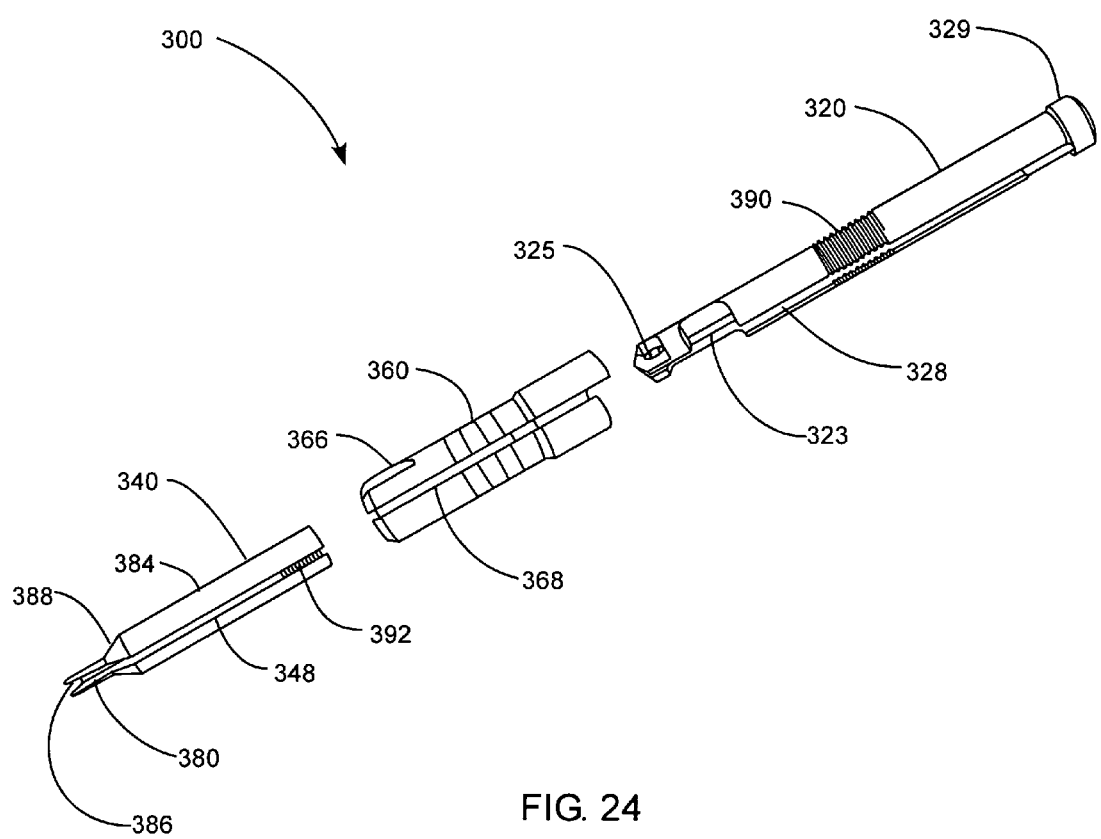
FIG. 24 is an unassembled perspective view of the knot tying device of FIG. 18, shown with the cord winding cylinder of FIG. 22.

Referring to FIGS. 18-20, the inner rod 320 can have an aperture 327 sized and shaped to receive a cord. For example, the aperture 327 can be located in an end 324 of the inner rod and can be a hole 325 extending into the inner rod. In another example, the aperture 327 can be a longitudinal slot 328 extending the length of the inner rod 320, and extending into an approximate center of the inner rod. In the case where the inner rod has both an aperture and a longitudinal slot, the aperture can be a hole extending through the end of the inner rod perpendicular or transverse to the axis of the longitudinal slot.

The hollow cylinder 340 can be rotatably disposable on the inner rod 320. Specifically, the hollow cylinder 340 can have a hollow interior space 352 that is sized and shaped to receive the inner rod 320. The hollow cylinder 340 can also have an aperture 347 extending from an outer surface 354 of the hollow cylinder to the interior space 352. The aperture 347 can be being sized and shaped to receive the cord 8 and allow the cord to extend through the hollow cylinder into the aperture in the inner rod. For example, the aperture 347 on the hollow cylinder 340 can be a longitudinal slot 348 extending the length of the hollow cylinder and extending through hollow cylinder from the outer surface 354 to the inner space 352.

The outer surface 354 of the hollow cylinder 340 can be configured to wind a cord on the outer surface. For example, the outer surface 354 can include a tip 380 disposed on an end 382 of a body cylinder 384. The tip 380 can be generally cylindrically shaped and have a relatively smaller diameter than the body cylinder 384. The tip 380 can also include an end notch 386 that can be sized and shaped to receive and hold the cord 8. The tip 380 and the notch 386 together can form a knot tying tip, indicated generally at 356 around which the cord 8 can be wound when tying a knot.

Additionally, the hollow cylinder 340 can include a substantially conical transition region 388 between the tip 380 and the body cylinder 384. The conical transition region 388 can define a ramp extending between the tip cylinder 380 and the body cylinder 384. The conical transition region 388, or ramp, can be sized and shaped to facilitate moving cord windings between the head cylinder and the body cylinder.

In use, the inner rod 320 can be positioned in interior space 352 to selectively align and misalign the aperture in the inner rod with respect to the aperture in the hollow cylinder. In an aligned position, the cord 8 can be inserted through the aperture in the hollow cylinder and extend into the aperture in the inner rod. The apertures 327 and 347 can then be misaligned to clamp the cord 8 between the inner rod and the hollow cylinder. In this way, the inner rod 320 and hollow cylinder 340 together can form a cord clamp.

After the cord is securely clamped, a knot can be tied by winding the cord around the hollow cylinder. When the knot is formed, the longitudinal slot 328 on the inner rod 320 and the longitudinal slot 348 on the hollow cylinder 340 can be aligned to form a continuous slot through the inner rod and the hollow cylinder. The cord 8 can then be inserted into the center of the windings through the continuous slot and the knot can be removed from the knot tying device by sliding the windings off an end of the hollow cylinder and lifting the cord out of the continuous slot. In the case where the aperture 327 in the inner rod 320 is a hole 325 that is separate from the longitudinal slot 328, the aperture 325 can then be aligned with the longitudinal slot 348 of the hollow cylinder 340 in order to release the cord clamp and remove the knot from the knot tying device 10.

The inner rod 320 can also be rotatably advanceable into the interior space 352 of the hollow cylinder 340. In one aspect, the inner rod 320 can include an external screw thread 390, and the hollow cylinder 340 can include a mating internal screw thread 392. In this way, as the inner rod 320 is rotated in the interior space 352, the external thread 390 engages the internal thread 392 and advances the inner rod 320 into the interior of the hollow cylinder 340. Thus, in one aspect, the inner rod 320 can be rotated within the hollow cylinder 340 in order to secure the inner rod in the hollow cylinder by a securing feature, such as screw thread 390 and 392. In another aspect, the inner rod 320 may be able to freely rotate and be advanced within the hollow cylinder 340 by pushing the inner rod into the interior space 352 of the hollow cylinder.

The inner rod 320 can also include an intermediate notch 323 disposed adjacent the longitudinal slot 328 at an intermediate location between the two ends 322 and 324. The notch 323 can be configured to hold an object to be tied into the windings of the knot. For example, the object held in the intermediate notch 323 can be a fish hook, and the intermediate notch can position the fish hook such that when the inner rod and hollow cylinder are twisted, the fish hook will be clamped into place in preparation for snelling the hook with the cord 8.

Additionally, the notch 323 can be used in conjunction with the slot 348 such that the cord can placed through the slot in the tip of the hollow cylinder and fed through the notch 323. When the notch 323 is misaligned with the slot 348, the notch 323 can form a cord cage that can hold the line in the knot tying device, but also allow the line to slide freely within the inner rod 320. Advantageously, this free motion of the cord facilitates winding the cord around the hollow cylinder 340 as discussed in greater detail below.

Figure 25:
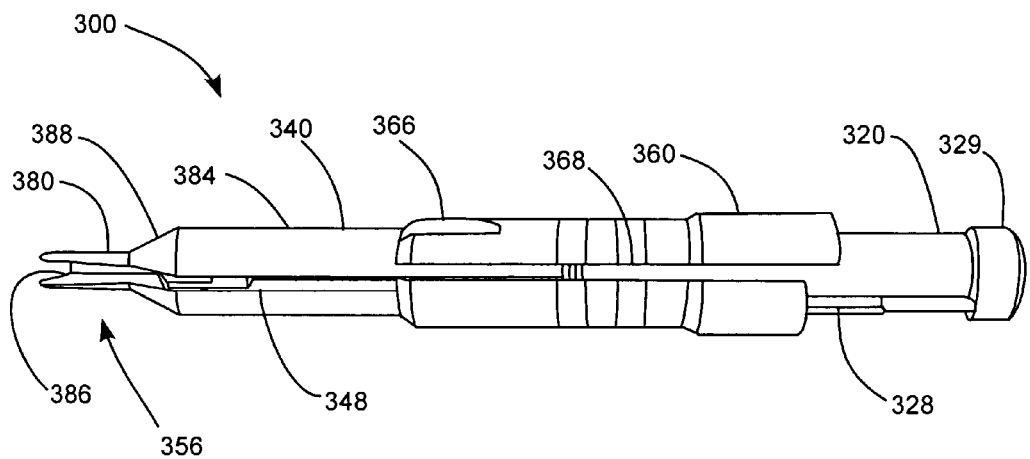
FIG. 25 is an assembled perspective view of the knot tying device of FIG. 18, shown with the cord winding cylinder of FIG. 22.
Figure 26:
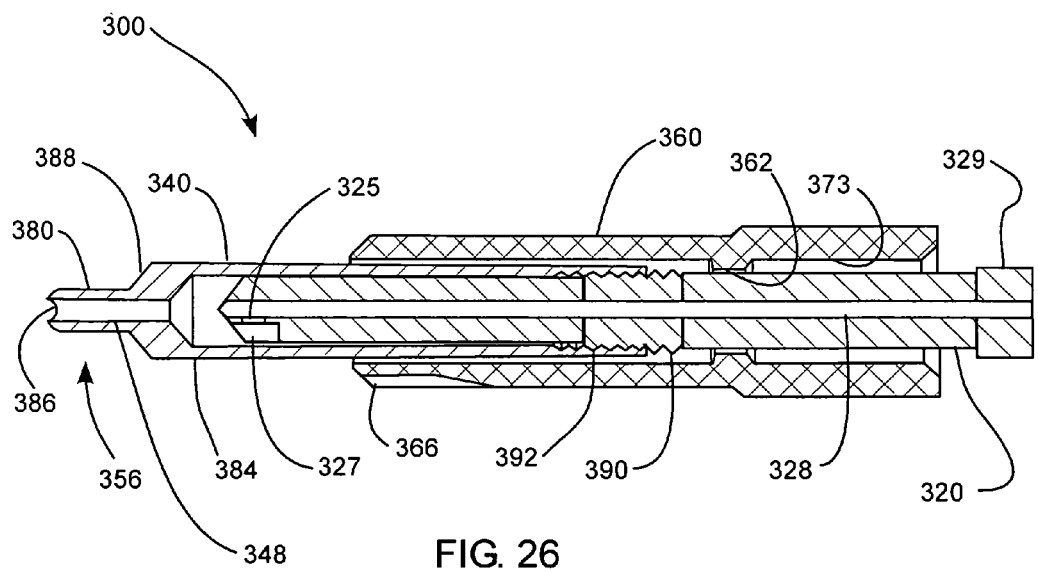
FIG. 26 is a cross section view of the assembled knot tying device of FIG. 18, shown with the cord winding cylinder of FIG. 22.

Referring to FIGS. 22-26, the knot tying device 300 can also include a cord winding cylinder 360. The cord winding cylinder can have a cord catch 366 that can catch and wind the cord 8 secured between the inner rod 320 and hollow cylinder 340 around the outer surface 354 of the hollow cylinder. The winding cylinder 360 can also have an internal stop 362 disposed at an intermediate location on the internal diameter 373 of the winding cylinder. The internal stop 362 can allow the winding cylinder 360 to slide longitudinally along the hollow cylinder 340 and the inner rod 320 between a pin head protrusion 329 and the interface 355 between the inner rod and the hollow cylinder. The cord winding cylinder 360 can be rotatably disposable on the hollow cylinder 340 and the inner rod 320, as shown in FIGS. 25-26.

In use, the cord winding cylinder 360 can be placed on either of the inner rod 320 or the hollow cylinder 340 and the other of the inner rod and hollow cylinder can be inserted into winding cylinder and joined together. In this way, the cord winding cylinder 360 can be restricted to free rotational and longitudinal movement between the pin head 362 and the interface 355 of the inner rod and hollow cylinder. Thus, when a cord 8 is secured in the knot tying device 10, the winding cylinder 360 can be rotated around the inner rod 320 and hollow cylinder 340 and the cord catch 366 can catch the cord and rotate it around the hollow cylinder to form helical windings on the hollow cylinder.

It will be appreciated that the knot tying device of the present invention is useful in many applications. For example, fishermen often need to repair or replace tackle in the course of fishing. Such a knot tying device can aid a fisherman to quickly and consistently form good nail knots or blood knots with which tackle, such as dry flies, hooks, or leader can be attached and used in fishing. Additionally, nail knots can successfully be used in surgical applications to secure implanted equipment within human tissue. The use of nail knots or blood knots in such applications allows a surgeon to secure an implanted device without having to attach a cord through an aperture on the device. Thus, such apertures can be eliminated from surgically implanted equipment. Advantageously, removing the aperture results in greater comfort to the patient since scar tissue and other tissues can't grow within the aperture.

Referring to FIGS. 27-31, the present invention provides for a method for forming a knot using a knot tying device 300, including placing an inner rod 320 with an aperture and a longitudinal slot 328 into a hollow cylinder 340 having a corresponding longitudinal slot 348. The hollow cylinder 340 can be rotatably disposed on the inner rod 320 to align or misalign the aperture and the longitudinal slots. The inner rod can be rotated within the hollow cylinder to align the aperture in the inner rod and the longitudinal slot in the hollow cylinder. A cord 8 can be placed through the longitudinal slot 348 in the hollow cylinder 340 and into the aperture 327 in the inner rod 320. The hollow cylinder 340 can be rotated with respect to the inner rod 320 to misalign the aperture 327 in the inner rod and the longitudinal slot 348 in the hollow cylinder 340 so as to clamp the cord 8 between the inner rod and an interior of the hollow cylinder, as shown in FIG. 27. The cord 8 can be extended around the hollow cylinder 340 and into a notch 386 in a tip cylinder 380 of the hollow cylinder with a segment 9 of the cord extending longitudinally along the tip cylinder, as shown in FIG. 28. The cord 8 can be wound around the hollow cylinder 340 to forming loops. The loops can form a helical winding circumscribing the segment 9 of cord extending longitudinally along the tip cylinder, as shown in FIG. 29. The longitudinal slots 328 and 348 of the inner rod 320 and the hollow cylinder 340 can be aligned to form a continuous longitudinal slot extending longitudinally along the knot tying device. The cord 8 can be pushed through the aligned longitudinal slots from an end opposite the tip end toward the tip end. The loops can be slid off the hollow cylinder, as shown in FIG. 30. The hollow cylinder can rotated with respect to the inner rod to unclamp the cord, and the cord can be tensioned to tighten the helical winding about the segment of the cord circumscribed therein, as shown in FIG. 31.

The method can also include placing a cord winding cylinder with a longitudinal slot on the hollow cylinder such that the cord winding cylinder can rotate about the hollow cylinder. The cord winding cylinder can then be rotated so that a cord catch on the cord winding cylinder catches the cord and winds the cord around the hollow cylinder to form the loops. The loops can form a helical winding circumscribing the segment of cord located within the internal hollow cylinder.

The method can also include placing an object, such as a fish hook, adjacent the segment of cord circumscribed by the helical winding so that the helical winding can be tightened about the object and the segment of cord circumscribed by the helical winding.

Referring to FIGS. 32-36, the present invention also provides for a method for forming a knot using a knot tying device 10 including an inner rod 20 with a longitudinal slot 28, a hollow cylinder 40 with a longitudinal slot 48, and a cord winding cylinder 60 with a longitudinal slot 68. The hollow cylinder and the cord winding cylinder can be rotatably disposed about the inner rod. A cord 8 can be clamped against the hollow cylinder at an end of the knot tying device. The cord 8 can be extended around the knot tying device 10 and into the inner rod at an opposite end of the knot tying device. The cord 8 can be drawn through the inner rod 20 to form a loop longitudinally around the knot tying device with a segment of the cord located within the internal hollow cylinder 40, as shown in FIG. 32. The cord winding cylinder 60 can be rotated so that a cord catch 66 on the cord winding cylinder catches the cord and twists the cord around the knot tying device forming loops on the outer hollow cylinder, as shown in FIG. 33. The loops can form a helical winding circumscribing the segment of cord located within the internal hollow cylinder. The longitudinal slots of the inner rod, the outer hollow cylinder, and the cord winding cylinder can be aligned to form a continuous longitudinal slot 70 that extends longitudinally along the knot tying device, as shown in FIG. 34. The loops can be slid off the knot tying device and away from the end of the cord that is clamped by the outer hollow cylinder, as shown in FIG. 35. The cord can be unclamped from the outer hollow cylinder. Tension can be applied to the cord to tighten the helical winding about the segment of the cord circumscribed therein, as shown in FIG. 36.

The method can also include rotating the internal hollow cylinder, the outer hollow cylinder, and the cord winding cylinder so the longitudinal slots are not in line with respect to one another. In this way the cord can be held within the hollow space of the inner rod.

The method can also include placing an object adjacent the segment of cord circumscribed by the helical winding so that the helical winding can be tightened about the object and the cord circumscribed by the helical winding.

The present invention also provides for a method for attaching a fish hook to a fishing leader cord including providing a knot tying device including an inner rod with a longitudinal through-slot, a hollow cylinder with a longitudinal through-slot, and a cord winding cylinder with a longitudinal through-slot. The hollow cylinder and the cord winding cylinder can be rotatably disposable about the inner rod. The longitudinal slots of the inner rod, the outer hollow cylinder, and the cord winding cylinder can be aligned to form a continuous longitudinal slot longitudinally along the knot tying device. A hook can be placed through the aligned longitudinal slots and into the notch in the internal hollow cylinder. The hollow cylinder can be twisted in relation to the inner rod to clamp the hook in the notch between the internal and outer hollow cylinders. A cord can be drawn through an eyelet of the hook. The internal and outer hollow cylinders can be rotated in the cord winding cylinder so that the cord twists the cord about itself. An end of the cord can be drawn through a loop of the cord formed near the eyelet by the twisted cord to form a knot. The cord can be tensioned to tighten the knot about the eyelet of the hook, and the hook can be unclamped from the notch in the internal hollow cylinder.

The present invention also provides for a method for snelling a fish hook including providing a knot tying device including an inner rod with a longitudinal through-slot, a hollow cylinder with a longitudinal through-slot, and a cord winding cylinder with a longitudinal through-slot. The hollow cylinder and the cord winding cylinder can be rotatably disposable about the inner rod. A cord can be clamped in the hollow cylinder at an end of the knot tying device. The cord can be extended around the knot tying device and into an opening in the inner rod at an opposite end of the knot tying device. The cord can be drawn through the inner rod to form a loop longitudinally around the knot tying device with a segment of the cord being located within the internal hollow cylinder. The cord can be rotated by the winding cylinder so that a cord catch on the cord winding cylinder catches the cord and twists the cord around the knot tying device forming loops thereon. The loops can form a helical winding circumscribing the segment of cord located within the internal hollow cylinder. The longitudinal slots of the inner rod, the outer hollow cylinder, and the cord winding cylinder can be aligned to form a continuous longitudinal slot longitudinally along the knot tying device. A small end of a hook can be placed through the slot and into the helical winding. The hook can be turned to orient a long end of the hook in the helical windings. The loops of the cord and the hook can be slid off the knot tying device away from the clamped cord. The cord can be unclamped from the outer hollow cylinder, and the cord can be tensioned to tighten the helical winding about the hook.

It is to be understood that the above-referenced arrangements are only illustrative of the application for the principles of the present invention. Numerous modifications and alternative arrangements can be devised without departing from the spirit and scope of the present invention. While the present invention has been shown in the drawings and fully described above with particularity and detail in connection with what is presently deemed to be the most practical and preferred embodiment(s) of the invention, it will be apparent to those of ordinary skill in the art that numerous modifications can be made without departing from the principles and concepts of the invention as set forth herein.

What is claimed is:

1. A knot tying device for tying knots in a cord, comprising:
    a) an inner rod having an aperture sized and shaped to receive a cord;
    b) a hollow cylinder rotatably disposable on the inner rod, and having an interior sized and shaped to receive the inner rod therein, and an aperture extending from an outer surface of the hollow cylinder to the interior, the aperture being sized and shaped to receive the cord therethrough, and the outer surface configured to wind the cord thereon; and
    c) the inner rod being positionable in the interior of the hollow cylinder to selectively align and misalign the aperture in the inner rod with respect to the aperture in the hollow cylinder such that the cord extending through the aperture in the hollow cylinder to the aperture in the inner rod is clamped between the inner rod and the hollow cylinder when the aperture in the inner rod is misaligned with the aperture in the hollow cylinder a cord winding cylinder, rotatably disposable on the inner rod and hollow cylinder around the hollow cylinder; the inner rod is rotatably advanceable into the interior of the hollow cylinder; Wherein the inner rod includes an external thread and the hollow cylinder includes a mating internal thread such that as the inner rod is rotated the external thread engages the internal thread to advance the inner rod into the interior of the hollow cylinder.

2. A knot tying device in accordance with 1, wherein the hollow cylinder further includes a tip disposed on an end of a body cylinder, the tip having a relatively smaller diameter than the body cylinder.

3. A knot tying device in accordance with 2, wherein the tip cylinder further includes an end notch sized and shaped to receive a cord therein.

4. A knot tying device in accordance with 3, wherein the hollow cylinder further includes a substantially conical transition region between the tip cylinder and the body cylinder, the conical transition region defining a ramp between the tip cylinder and the body cylinder sized and shaped to facilitate moving cord windings between the tip cylinder and the body cylinder.

5. A knot tying device for tying knots in cord, comprising:
    an inner rod, having a longitudinal slot;
    an intermediate hollow cylinder, rotatably disposable on the inner rod, and having a longitudinal slot from an outer diameter to a hollow interior;
    the intermediate hollow cylinder being rotatable on the inner rod to selectively align or misalign the slot in the inner rod with respect to the slot in the hollow cylinder to form a cord clamp therebetween when the slots are misaligned;
    a cord winding cylinder, rotatably disposable on the intermediate hollow cylinder and longitudinally slidable thereon, and having a longitudinal slot; and
    a cord catch disposed on the cord winding cylinder and configured to catch a cord secured between the inner rod and the intermediate hollow cylinder and wind the cord around the outer hollow cylinder; wherein the internal rod has an external screw thread and the intermediate hollow cylinder has a corresponding internal screw thread such that the intermediate hollow cylinder threads onto the inner rod, and the inner rod is rotatably advanceable along a longitudinal length of the intermediate hollow cylinder.

6. A device in accordance with claim 5, wherein the cord clamp includes an aperture formed in an end of the inner rod, transverse to the longitudinal slot, such that when the intermediate hollow cylinder is disposed on the inner rod, the intermediate hollow cylinder can be 10 rotated on the inner rod to:
  i) align the aperture with the slot on the intermediate hollow cylinder to allow a cord to be placed through the slot and into the aperture; and
  ii) misalign the aperture with the slot on the intermediate hollow cylinder to clamp the cord between the inner rod and intermediate hollow cylinder.

7. A device in accordance with claim 5, wherein the intermediate hollow cylinder further includes:
  a smaller end with a relatively smaller diameter with respect to a larger end of the intermediate hollow cylinder diameter; and a notch formed in the smaller end, the smaller end and notch together forming a knot tying tip around which a cord is wound when tying a knot on the knot tying device.

8. A device in accordance with claim 5, wherein the inner rod further includes an intermediate notch disposed adjacent the longitudinal slot at an intermediate location between a head end and a tail end, the notch being configured to hold a fish hook.

9. A device in accordance with claim 5, wherein the longitudinal slots of the inner rod, the intermediate hollow cylinder, and the cord winding cylinder are rotatably alignable to form a continuous slot between a head end and a tail end of the knot tying device, the continuous slot being sized and shaped to allow a cord to pass through the slot and escape the knot tying device.

10. A device in accordance with claim 5, wherein the cord catch further includes a protrusion formed longitudinally on an outer diameter of the cord winding cylinder.

11. A device in accordance with claim 5, wherein the cord catch further includes an indentation extending longitudinally along the cord winding cylinder.

* * * * *